(12) United States Patent
Wismüller

(10) Patent No.: US 9,189,846 B2
(45) Date of Patent: Nov. 17, 2015

(54) METHOD AND DEVICE FOR REPRESENTING MULTICHANNEL IMAGE DATA

(76) Inventor: Axel Wismüller, Simbach am Inn (DE)

( * ) Notice: Subject to any disclaimer, the term of this patent is extended or adjusted under 35 U.S.C. 154(b) by 1527 days.

(21) Appl. No.: 12/160,528
(22) PCT Filed: Jan. 8, 2007
(86) PCT No.: PCT/EP2007/000099
§ 371 (c)(1), (2), (4) Date: Mar. 19, 2010
(87) PCT Pub. No.: WO2007/082650
PCT Pub. Date: Jul. 26, 2007

(65) Prior Publication Data
US 2010/0166273 A1 Jul. 1, 2010

(30) Foreign Application Priority Data
Jan. 12, 2006 (DE) .......................... 10 2006 001 681

(51) Int. Cl.
G06K 9/62 (2006.01)
G06T 7/00 (2006.01)
(Continued)

(52) U.S. Cl.
CPC ............... *G06T 7/0012* (2013.01); *G06T 19/00* (2013.01); *A61B 6/4241* (2013.01); *G06T 15/503* (2013.01); *G06T 2207/30004* (2013.01); *G06T 2210/41* (2013.01)

(58) Field of Classification Search
CPC .................................................. G06T 15/503
USPC .......................................................... 382/128
See application file for complete search history.

(56) References Cited

U.S. PATENT DOCUMENTS 6,540,681 B1 * 4/2003 Cheng et al. ................... 600/443
2004/0052328 A1 * 3/2004 Sabol et al. ...................... 378/37
2004/0252873 A1 12/2004 Avinash et al.

FOREIGN PATENT DOCUMENTS

EP 1365385 B1 * 11/2003

OTHER PUBLICATIONS

Song, et al. "Simultaneous Acquisition of Multiple Resolution Images for Dynamic Contrast Enhanced Imaging of the Breast." Magnetic Resonance in Medicine 46: 503-509. 2001.*

(Continued)

*Primary Examiner* — Anita Coupe
(74) *Attorney, Agent, or Firm* — Hooker & Habib, P.C.

(57) ABSTRACT

The invention relates to a method for display of multi-channel image data, characterized in that multi-channel image data of an object that are provided by multiple channels of an imaging device are received, an image synthesis is performed on the basis of the multi-channel image data, and a synthesized image data set is output on a display device, characterized in that the image synthesis is performed in a way that the single-channel image data are temporally shifted according to a given function and the parameters of the given function are controllable by a user during the output of the synthesized image data set on the display device. Furthermore, the invention relates to a device for display of multi-channel image data with an appliance for receiving multi-channel image data of an object that are provided by multiple channels of an imaging device, a computation unit for the execution of an image synthesis which is performed on the basis of the multi-channel image data, and an output unit for the display of synthesized image data sets, characterized in that the computation unit is designed in a way that for the image synthesis the single-channel image data are temporally shifted according to a given function and parameters of the given function are controllable by a user during the output of the synthesized image data set on the display device.

22 Claims, 1 Drawing Sheet

(51) Int. Cl.
    *G06T 19/00* (2011.01)
    *G09G 5/397* (2006.01)
    *G06T 15/50* (2011.01)
    *A61B 6/00* (2006.01)

(56) References Cited

OTHER PUBLICATIONS

Hermann, Andreas et al. "Oscillating Intensity Display of Soft Tissue Lesions in MRI", IEEE Transactions on Medical Imaging, vol. M1-6, No. 4, pp. 370-373, Dec. 1987.*

Twellmann et al., "An adaptive extended colour scale for comparison of pseudo colouring techniques for DCE-MRI data", http://www.techfak.uni-bielefeld.de/ags/ni/publications/media/TwellmannLichteSaalbachWismuellerNattkemper2005-ACC.ps.gz, XP-002407822, Mar. 2005.

Nattkemper et al., "Tumor feature visualization with unsupervised learning", Medical Image Analysis, Oxford University Press, Oxford, GB, vol. 9 No. 4 Aug. 2005, pp. 344-351, ISSN: 1361-8415, XP-004947779, May 19, 2005.

* cited by examiner

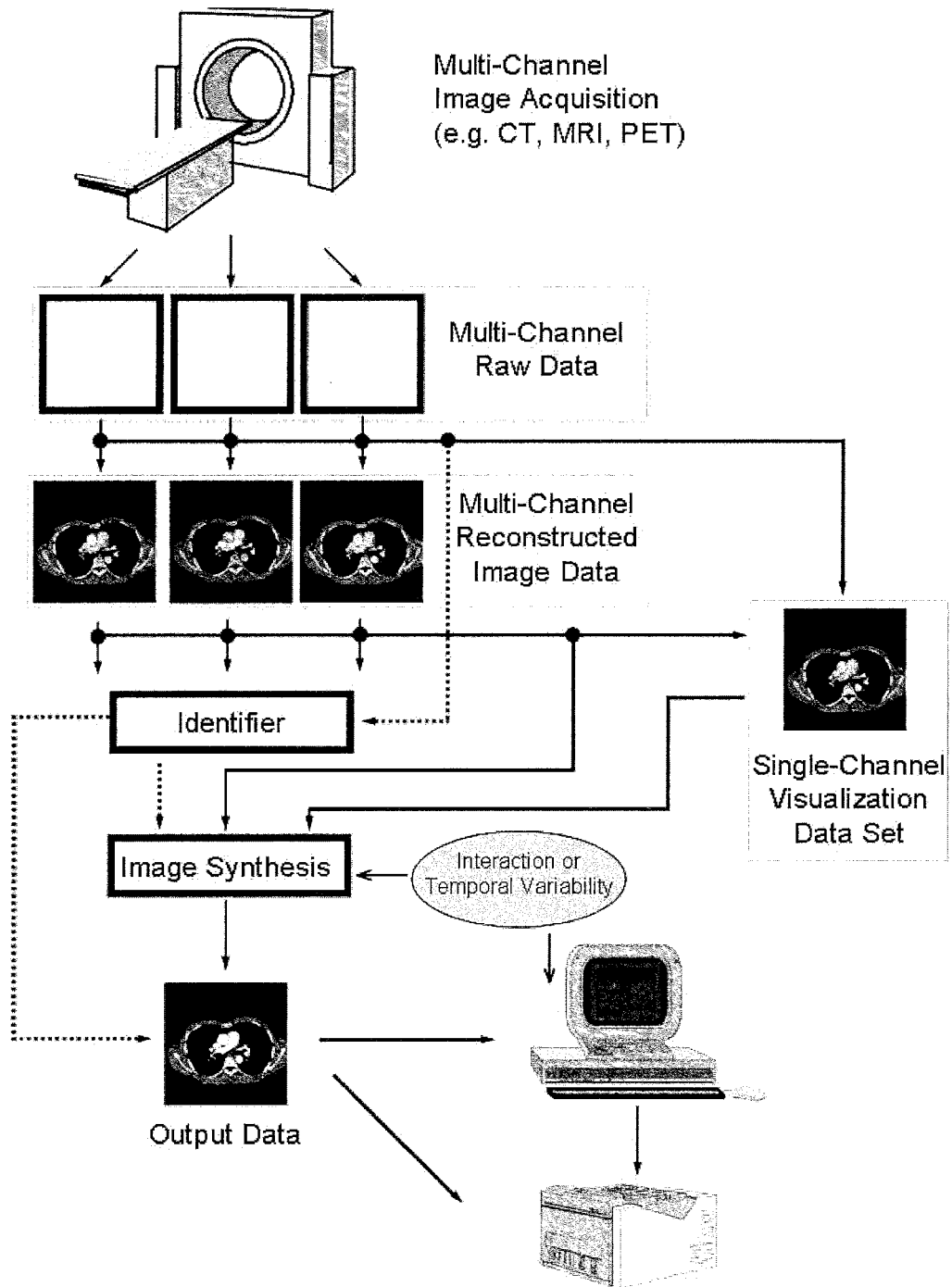
Scheme for description: The dashed line relates to embodiments, in which an identifier is used, the gray „Interaction or Temporal Variability" relates to embodiments, where the parameters of the image synthesis and/or of the output device are variable, specifically controllable by users or temporally variable.

METHOD AND DEVICE FOR REPRESENTING MULTICHANNEL IMAGE DATA

The present invention refers to a method and a device for the display of multi-channel image data. According to one aspect the invention provides a method for display of multi-channel image data according to claim 1. According to a second aspect the invention provides a device for display of multi-channel image data. Further aspects result from the following description and the drawings, specifically the description of preferred embodiments of the invention.

1. ECONOMIC-TECHNICAL RELEVANCE AND MEDICAL RELEVANCE

In recent years, biomedical imaging methods have moved into the focus of interest, by which multiple image data sets are simultaneously acquired in equivalent object position, where altered physical parameters or even different physical image acquisition methods are applied for the individual data sets.

Multidimensional image data sets (multi-channel image data sets) result from this, in which each location within the image is characterized by more than only one single number.

Explicitly, only two examples should be mentioned here: Energy-resolved computer tomography (e.g. as Dual Source CT or as CT with energy-selective detectors) and the acquisition of MR data, from which images with different signal characteristics (e.g. T1-, T2-, PD-weighting) can be reconstructed, i.e. for each location within the image, multiple physical parameters can be simultaneously determined (e.g. by application of True-FISP inversion recovery sequences).

One is hoping that by simultaneous analysis of all input channels in such multidimensional data sets one can obtain more information about the imaged object than would be possible by the isolated analysis of single-channel images. Methods for extraction and visualization of such profitable additional information, however, have not yet been introduced into medical practice to a significant extent.

The above sketched approach for the acquisition of multi-channel image data sets could achieve a significant economic importance, as one is hoping to reduce the dose of externally applied contrast agent, i.e. elevate its detection threshold, by utilization of complementary image information from different input channels. Here, on one hand, contrast agents containing iodine that are applied intravenously during the acquisition of computer-tomographic recordings, are currently of specific practical relevance in medical imaging, on the other hand, contrast agents containing gadolinium that are applied in magnetic resonance tomography.

A thus reduced detection threshold for contrast agent offers significant medical advantages. Although these are not a subject of the present patent application, they are important for the understanding of the technical-economic relevance. Namely, by a dose reduction of the above mentioned contrast agents, their adverse effects in patients can be reduced, and patients, in which the application of contrast agent appears to be contraindicated so far, could be examined as well. A typical example is the dose-reduced application of iodinated contrast agents in computer tomography in patients with function deficits of the kidneys.

Every even little improvement of the detectability of such contrast agents would, thus, have enormous economic consequences for the contrast agent market and is a threat for the existence of companies that have specialized on the production and marketing of such contrast agents. Vice versa, a profit could emerge for medical technology industry, as the increased detectability of contrast agents must be paid for by the purchase of devices applicable to this.

In the following, a method is described that allows to extract a diagnostic benefit from the information of multi-channel data sets in medical practice.

Initially, the invention is described by means of a typical example. For reasons of simplicity and comprehensibility, a specific case is forestalled. Multiple generalizations and specifications are stated in the subsequent paragraphs.

2. TYPICAL SCENARIO

Step 1:
Initially multi-dimensional, i.e. multi-channel image data are collected, e.g. by multi-energy computer tomography, by recording image data sets from the same patient in equivalent object position with different tube voltages in a simultaneous or temporarily consecutive manner. A reconstruction to image data sets is performed, where in the specific case of dual-energy computer tomography, typically the location-specific X-ray absorption for two different energy ranges (tube voltages) is computed. From this, in the simplest case, two image data sets are obtained that represent a bi-spectral data set, i.e. for each location within the image, there exist two X-ray absorption values.

Step 2:
In a second step, a detection or identification of contrast agent is carried out. To this end, the location-specific X-ray absorption values of the bi-spectral data set are entered into an identifier that computes estimates for the location-specific presence and/or the location-specific concentration of contrast agent.

Step 3:
In a next step, the output of the identifier is used to synthesize a new image data set, in which the brightness values of the pixels are modified, typically up-scaled, by using tie output of the identifier, i.e. pixels, at which the identifier has recognized the presence of contrast agent or has determined a specific concentration, are assigned to a higher gray level.

Step 4:
Finally, this synthetic image is displayed on a suitable display device and can there also be manipulated, e.g. related to window settings by user control.

Step 3a:
As an alternative to steps 3 and 4, the two image data sets can be output simultaneously (superimposed) on a suitable output device, e.g. on the monitor of a viewing station of a PACS system, where an image data set is synthesized, for which the information of the two image data sets is used. In particular, the display of the two image data sets can be modified controlled by the observer, or can be variable over time, e.g. according to a given pattern.

A scheme for method and device for the sequence of the above steps is presented in FIG. 1.

3. DETAILED DESCRIPTION

By the method or the device multidimensional, i.e. multi-channel image data or raw data, from which multidimensional image data can be calculated, are processed and visually displayed. Here, explicitly image data sets from the following modalities should be mentioned: Computer Tomography (CT), Magnetic Resonance Tomography (MRI), Positron Emission Tomography (PET), Single Photon Emission Computed Tomography (SPECT), optical coherence tomography, ultrasound, conventional projection radiography. "Multidimensionality" or "multi-channel" states that at a pixel not only a single scalar image information is present (e.g. a single signal intensity, a single value for the local X-ray absorption, etc.), but that one can characterize each location in the image by more than a single number. In general, image data sets are concerned, in which the properties of each pixel are indicated by more as a single real number in the sense of a vector of real numbers $$\vec{a}(x, y, z) = \begin{pmatrix} a_1(x, y, z) \\ \vdots \\ a_n(x, y, z) \end{pmatrix}, a_i(x, y, z) \in \mathcal{R}, i \in \{1, \ldots n\}, n \in N,$$

where N denotes the set of natural numbers, x, y, z the spatial coordinates of the respective pixel. It should be mentioned that the terms "pixel", "image point", and "voxel" are used as synonyms independently of the dimensionality of the image data set.

Included special cases specifically cover situations, in which the $a_i$

- are temporally consecutively recorded or computed values (in the sense of so-called "4D data sets"), e.g. recorded temporal sequences of image data sets under variation of experimental conditions (e.g. functional MR tomography)
- or represent temporally consecutively recorded or computed values after administration of contrast agent and/or radionuclides (dynamic multi-phase CT, MRI, PET, SPECT, contrast-enhanced MEI, e.g. perfusion MRI, contrast agent dynamics)

and/or

- different acquisition techniques have been applied, e.g. different tube voltages in multi-energy CT, different energy ranges of the detected radiation energy in energy-resolved detectors, different tube currents or mAs products in X-ray or CT methods, different choice of acquisition parameters within the same modality, e.g. in case of the acquisition of MRI data sets (e.g. combination of data acquired in T1-, T2-, and PD weighting) or the combined application of different acquisition modalities, specifically PET-CT or PET-MR. Here, both image data sets are concerned that have been recorded by combination devices and image data sets that have been acquired by different devices and are subject to a subsequent image data registration. In the field of MRI, the following should be explicitly mentioned: Methods in which, for each location of the imaged object, multiple physical parameters are measured (e.g. by True-FISP inversion recovery sequences), diffusion sequences with different parameters (e.g. b-values). Finally, nuclear medicine methods with simultaneous or temporally shifted application of different radionuclides and/or energy-resolving detectors should be mentioned.

It should be emphasized that is irrelevant for method and device, whether the further steps occur on the basis of multi-channel raw data or multi-channel reconstructed image data.

Specifically, methods and devices for display of data from the following image acquisition modalities should be mentioned:

Energy-resolved CT, specifically Dual or Multiple Source CT (specifically also, if equipped with multi-row detectors or flat-panel detectors), where at image data acquisition two or more X-ray sources are operated in a simultaneous or temporally shifted way, in particular, if the different X-ray sources are operated with different physical parameters, specifically different tube voltage and/or tube current (or different mAs product). Analogously, this description also holds for methods and devices, where the X-ray radiation is generated at locally different focal spots within the X-ray tube in a simultaneous or temporally shifted, specifically alternating (so-called "flying spot" or "z-sharp" technology) manner, in particular, if the energy spectrum and/or the radiation intensity for the different focal spots is different.

Computer tomography with energy-selective detectors: here, the radiation received by each detector element is resolved into at least two different energy ranges, for example in a way that by application of beam-hardening filters (e.g. copper) a somewhat modified (hardened) radiation with regard to its spectral composition is collected after passage through a first detector through further detectors arranged behind it, or that the sensitivity characteristic of the detectors for the detection of radiation of different energy ranges is temporally varied. This results in the possibility to reconstruct image data sets that take into account the location-specific X-ray absorption in different energy ranges.

It is irrelevant for the invention whether the determination of the energy-specific data sets and/or the subsequent processing steps (identification, image synthesis) is performed directly based on CT raw data (e.g. in the sense of energy- or X-ray source-specific sinograms), or whether image data are initially reconstructed by separated utilization of the individual detector channels or X-ray specific signals.

MRI with multidimensional image data acquisition: Methods in which multiple physical parameters can be measured for each location of the imaged object (e.g. by True-FISP inversion recovery sequences), diffusion sequences with different parameters (e.g. b-values), temporally consecutive or simultaneous acquisition of data with different signal characteristics with regard to repetition time, echo time, or other MRI sequence parameters or different sequence types.

Dynamic MRI, CT, PET, SPECT, optical methods, ultrasound, where data sets are recorded in a temporally successive way, specifically after administration of contrast agent or in case of temporally variable recording conditions (e.g. so-called functional MRI).

Particularly emphasized should be multidimensional image data sets, in which contrast agent is applied in a reduced dose compared to the usual dose for non-multichannel image data acquisition. Here, the detectability of contrast agent can be enhanced by the multi-dimensional image data acquisition, whereby less contrast agent has to be administered. Specifically to be mentioned here: Intravenous application of iodinated contrast agents in CT and X-ray examinations as well as the intravenous application of gadolinium-containing contrast agents in MRI.

Multidimensional image data sets from multi-energy CT (Dual or Multiple Source CT or CT with energy-resolving detectors, see above), where specific contrast agents are applied, namely iodinated contrast agents as well as contrast agents that contain atoms with atomic numbers greater than the atomic number of Iodine, specifically Xenon, Barium, or Gadolinium.

Multidimensional image data sets from MRI, where specific contrast agents are applied: contrast agents that contain Gadolinium or iron oxide particles.

Multidimensional image data sets that are obtained by methods or devices for X-ray detection by charge integration and/or photon counting, e.g. in the sense of "counting and integrating readout", as e.g. described in the publications [4,5]. Here, it is irrelevant whether such an X-ray detection is used in the framework of projection radiography, angiography, or computer tomography.

Multidimensional image data sets that are generated using methods or devices for the generation of X-rays that do not require a thermoelectric emission of electrons from the cathode material, e.g. by use of carbon nanotubes, as e.g. analogously to the generation of X-rays described in publication [6].

It is also irrelevant for the invention, whether the image data acquisition, image synthesis and/or image data visualization are performed in an spatially and/or temporally separated manner.

In the entire description, the terms "image" and "image data set" are used as synonyms. Specifically, it is not differentiated between 2D images and 3D data sets in the description and the claims.

It should be noted that the invention does not only include imaging in biomedical applications, but e.g. also imaging for security applications, in particular, CT, X-ray, MRI, ultrasound, optical methods for security checks, testing of materials, and customs applications as well as acquisition of multispectral data in satellite remote sensing.

According to preferred examples of carrying out the invention, the multidimensional data sets are, in a second step, conveyed to an identifier that computes an estimate for location-specific properties of the examined object, e.g. the location-specific presence and/or the location-specific concentration of certain substances. Here, it is irrelevant, whether raw data or already reconstructed images are used in order to compute such estimates. In the simplest case, already reconstructed multidimensional image data are on hand as input of the identifier. In particular, it is possible that the identifier computes its output data not only based on pixel- or voxel-specific image properties, but that image properties of the pixel- or voxel-neighborhood or also global image information is utilized.

The identifier can be made up in different ways. In the simplest case, it represents a classifier or function approximator, in which, for each pixel, the pixel-specific vector (e.g. of the signal intensities or gray values of the single channels) is entered, and from this the estimate for the location-specific presence and/or the location-specific concentration of specific substances or the location-specific value of physical, chemical or biological properties of the examined object is computed.

Examples for such identifiers are various kinds of linear and non-linear classifiers or function approximators, neural networks, e.g. multi-layer perceptrons, e.g. trained by "error back-propagation"), Radial Basis Functions networks, Support Vector Machines, local models, various kinds of nearest-neighbor classifiers, rule-based classifiers, processing by arbitrary mathematical operations, e.g. difference calculation or weighted summation of the input channels, threshold value operations, vector quantizer, clustering algorithms, e.g. learning vector quantization (LVQ), self-organizing maps (SOM), exploratory morphogenesis (XOM), genetic or evolutionary algorithms. Specifically all methods should be mentioned here that are quoted in standard works of neuroinformatics and pattern recognition, e.g. [1], [2], [3].

For the computation of the estimates, non-local, i.e. comprising more than one pixel, image features can be used (filters, edge enhancement, arbitrary pre-processing) as well.—It is only essential that the information of more than one single channel (or raw-data channel) is used for the computation of the estimates.

As a result, the identifier provides estimates for the location-specific presence and/or the concentration of specific material properties or substances, e.g. presence or concentration of contrast agent. This result is output (or stored, e.g. in DICOM format, or transferred, e.g. to a PACS system) or used in a next step to synthesize a new image data set, in which the features of pixels (specifically gray values, colour, transparency, luminance) are determined based on it, where optionally the multi-channel raw data, the multi-channel reconstructed image data, or a single-channel visualization data set, or arbitrary combinations thereof, are used together with the output of the identifier in order to synthesize the output image data set.

For the special case of the detection of contrast agent, it is possible to attribute, depending on the output of the identifier, those pixels with a modified pixel feature (e.g. an increased gray value or a changed colour, transparency, luminance), at which contrast agent has been identified or a high estimate for the concentration of contrast agent has been determined. Here, it is e.g. possible, depending on the probability of the presence of contrast agent or depending on the estimated concentration of the contrast agent, to change the image data sets in a way, that image locations with a high probability or a high concentration are visible more clearly, e.g. by higher gray values.

As a preferred embodiment the following approach for the energy-resolved CT (Dual or Multiple Source CT or CT with energy-resolving detectors) should be described: Let n be the number of used energy channels. Either, in a first case, an image reconstruction is performed that does not only utilize the information of a single energy channel, but of multiple energy channels, or, in a second case, n image data sets are reconstructed initially from the n single energy channels, i.e. for the reconstruction of a single image data set only the information of a single energy channel is utilized at a time.

(Alternatively, it is also possible to calculate different image data sets, where for the calculation of the individual data sets the information of the raw data of multiple energy channels is utilized, however, the energy-resolved image data acquisition leads to a situation in which the computed image data sets differ from each other. For example, multiple image data sets that each represent the absorption properties of (almost) "monochromatic" X-ray radiation, e.g. with energies of 80 kV, 90 kV, 100 kV, 110 kV, 120 kV, 130 kV, 140 kV, could be calculated from the combined utilization of two raw data sets that have been recorded with tube voltages of 140 kV and 80 kV. The number n of channels of the raw data does not necessarily have to correspond to the number of channels m of the reconstructed image data.)

In both cases, the computation of an image data set (henceforth called visualization data set) that takes into account the information of more than a single input channel. In the first case, this results already from the reconstruction, in the second case, after completed reconstruction, a new visualization data set can be calculated based on the reconstructed images of the individual channels. Here, a primitive method would be the arithmetic averaging of the gray values of the image data reconstructed from the individual channels, however, arbitrary algorithms are thinkable, as long as they utilize the information of more than an individual single channel respectively, specifically PCA, XOM, SOM. For the invention it is irrelevant, whether the image calculations are performed on an image-, console-, or side-console computer of the CT system or on an arbitrary different computer, e.g. of a PACS system or a special server.

As a preferred embodiment, the following approach is to be mentioned here: The pixel-specific features (gray values, colours, luminance, transparency) of the single-channel visualization data set are modified based on the output of the identifier, where a new image data set is generated, which is visually displayed, stored, or transferred. Alternatively, the visualization data set can be transmitted or stored, separated from the output of the identifier, where the information of both data sets is combined, e.g. superimposed, for the purpose of visualization or graphical output, not before a later point in time or at a different place.

Furthermore, specific embodiments are methods and devices, where the output data of the identifier in combination with the visualization data set, or the output data of the identifier in combination with the single-channel data, or the output data of the identifier with the visualization data set and the single-channel data (specifically in DICOM format), are stored, transferred to a computer network, in particular, a PACS system, or, visualized, specifically in a mutually superimposed way.

A typical situation would be the following: The image data acquisition is, for example, performed after administration of a reduced contrast agent dose compared to the conventional approach. A visualization data set is generated from the multi-channel raw data or multi-channel reconstructed image data. Furthermore, single-channel-specific raw and image data are utilized to compute estimates in an identifier for the probability of the location-specific presence or the location-specific concentration of contrast agent.

The output data of the identifier are stored, just as the image data, in DICOM format or transferred into a PACS system. On the console computer of the imaging device or the viewing stations of the PACS system, a graphical output is performed, where the visualization data set and the output data of the identifier or an image data set synthesized from both data sets is displayed. Here, for example, those pixels, at which a high contrast agent concentration has been identified, are up-scaled with regard to their gray values, so that the image impression of an examination with a higher contrast-agent dose is generated.

The description presented above for the energy-resolved CT applies to every other multi-channel imaging modality, all CT-specific terms are to be replaced in the description correspondingly. In particular, the description is analogously transferable to MRI in the case of utilization of different acquisition sequences or image contrasts.

After completed image synthesis, the output data (these consist of the identifier's output or a synthesized image data set, which has been computed based on the identifier's output, a single-channel visualization data set and/or the multi-channel raw- or reconstructed image data sets, or arbitrary combinations of the mentioned data sets) are optically output (e.g. on the monitor of an operating- or post-processing console of the image acquisition device, on the monitor of a viewing station of a PACS system, on the monitor of an arbitrary computer, on which a biomedical image data viewer has been installed, e.g. a DICOM viewer, on a projector or a printer). For synthesized image data sets, it is irrelevant, in which parts of a computer they have been calculated, in particular, whether these have been already calculated in the CPU, or in a graphics chip immediately before output. It is also important to mention that the presence or the utilization of an identifier is not absolutely required for the image synthesis.

A specific embodiment is a situation, in which during the output (or on a print-out) it is indicated that it is a synthesized image data set, or parameters of the image synthesis or input data utilized for the image synthesis or their type or properties are displayed. Such displays can, for example, be carried out by text annotations superimposed on the images, colour marks, or graphical symbols. Furthermore, methods and devices should be mentioned as specific embodiments, where the output images can be manipulated, specifically by user control, specifically by window modification, alteration of contrast or image brightness, colour, luminance, transparency, etc. Furthermore, methods and devices should be mentioned as specific embodiments, where the parameters of the input data of the image synthesis are temporally variable or can be influenced or controlled by user interaction, e.g. the weighting of input data channels, e.g. interactive or temporally variable, e.g. oscillating, alpha-blending. For the options for user-controlled influence, specifically computer mice (eventually specifically developed for this purpose), joy sticks, touch screens, and keyboards should be mentioned.

A specific situation encompasses methods and devices, where image data are output from multi-channel image data acquisitions simultaneously, e.g. superimposed, on an output device, also without utilization of an identifier, characterized in that the display on an output device can be influenced or controlled by the user or is temporally variable.

Here, the image synthesis can be performed: from the multi-channel raw data, the multi-channel reconstructed image data, from a single-channel visualization data set and/or the output of an identifier in the sense described above. Here, the involvement of such an identifier is, however, optional as well.

Here, also embodiments should be mentioned, where during the output (or on a print-out) it is indicated that it is a synthesized image data set, or parameters of the image synthesis or input data utilized for the image synthesis or their type or properties are displayed. Such displays can, for example, be carried out by text annotations superimposed on the images, colour marks, or graphical symbols. Furthermore, methods and devices should be mentioned as specific embodiments, where the output images can be manipulated, specifically by user control, specifically by window modification, alteration of contrast or image brightness, colour, luminance, transparency, etc. Furthermore, methods and devices should be mentioned as specific embodiments, where the parameters of the input data of the image synthesis are temporally variable or can be influenced or controlled by user interaction, e.g. the weighting of input data channels, e.g. interactive or temporally variable, e.g. oscillating, alpha-blending. For the options for user-controlled influence, specifically computer mice (eventually specifically developed for this purpose), joy sticks, touch screens, and keyboards should be mentioned.

For temporally variable image synthesis or output, a temporally oscillating alpha-blending should be mentioned for example, specifically also in a situation, where its parameters, specifically the oscillation frequency, is controllable by the user. If, for example, a multidimensional image data set $$\vec{a}(x, y, z) = \begin{pmatrix} a_1(x, y, z) \\ \vdots \\ a_n(x, y, z) \end{pmatrix}, a_i(x, y, z) \in \mathcal{R}, i \in \{1, \ldots n\}, n \in N$$

is used as input, where n shall represent the number of individual channels, (N: the set of natural numbers) and x, y, z the spatial coordinates of the respective voxel, the output s(x, y, z) at the voxel (x, y, z) at time t could, for example, be computed by:

$$s(x, y, z) = \sum_i w_i(t) a_i(x, y, z) \text{ with } w_i(t) = p_i \sin(\omega_i t),$$

where $p_i, \omega_i \in \mathfrak{R}$ can also be chosen in a pixel-specific and/or temporally variable, specifically also influenceable by user control, manner. It should be emphasized that arbitrary patterns of temporal variability, i.e. arbitrary temporally variable functions can be chosen for the image synthesis, specifically also non-periodic, non-continuous, non-differentiable ones. Also, mappings that can be varied temporally based on random numbers, are permitted, and shall be included here as patterns of temporal variability. Let $b_i$ be the channels of the input data of the image synthesis (images or raw data), then all mappings $f(b_i, t)$ are thus included, where $f$ is an arbitrary function in a mathematical sense that also depends on time t.

4. FORMAL DESCRIPTION

Finally, as a supplement for the description, a glossary should be formulated, which characterizes the components of the invention according to FIG. 1:

Multi-channel image data acquisition: Conceivable alternatives for the acquisition of multi-channel image data have already been drafted above. A special variant is that multi-channel data are generated by performing arbitrary image processing operations (e.g. arbitrary filtering, e.g. edge enhancement), where the result can again be interpreted as an image data set. The combination of the original single-channel data together with the result of the image processing operation can then be interpreted as a multi-channel data set.

Multi-Channel Raw Data:

In preferred embodiments, these consist of angle-dependent radiation intensity values measured by CT detectors, which can be represented as so-called "sinugrams", or signal intensity values detected by RF receivers in MRI devices. I.e., arbitrary data are concerned, from which image data sets can be reconstructed.

Multi-Channel Reconstructed Image Data:

These refer to image data that are obtained on the basis of the raw data. For multi-channel raw data, it is not required that the information of exactly one raw data channel is utilized of one image data channel. An image data channel can also be computed on the basis of the information of multiple raw data channels. For the further steps, it is also not necessarily required that the image data can be reconstructed explicitly. The following identification and/or image synthesis can be performed on the basis of the raw data as well.

Single-Channel Visualization Data Set:

Such a single-channel image data set for the purpose of visualization is characterized in that it is calculated on the basis of the information of more than one raw- or image data channel.

Identifier:

The identifier receives the information of more than one raw- or image data channel as input. From this, it calculates location-specific properties of the examined object, e.g. estimates for the probability and/or location-specific concentration of specific substances or the location-specific presence or the strength of physical, chemical, or biological properties. The output of the identifier can serve as input for the synthesis of a new image data set or can, in itself, be seen as output of the system, which can be stored, transmitted, or output via a suitable output device, e.g. graphically displayed.

Image Synthesis:

For a first alternative, this is performed on the basis of the output of the identifier, where a new image data set is generated on the basis of:

Output of the identifier,

Output of the identifier and a single-channel visualization data set,

Output of the identifier and multi-channel raw-data, or

Output of the identifier and multi-channel reconstructed image data.

For a second alternative, an identifier is not necessarily required, i.e. the image synthesis can also only be performed on the basis of the multi-channel raw data, of multi-channel reconstructed image data, a single-channel visualization data set, or arbitrary combinations thereof.

Output Data:

These are the result of the image synthesis or, optionally, as a special alternative, the output of the identifier without subsequent image synthesis. The output data can be stored (e.g. in the DICOM format common in medical imaging), transferred into a computer network (e.g. in the sense of a PACS system), or output, e.g. on the monitor of an arbitrary computer, specifically of a main- or side-console-computer of an imaging device, on the monitor of a viewing station of a PACS system, or of a computer linked to a PACS system. An output can also be carried out as a print-out (e.g. on film- or paper printers), or a display can be performed using a wide range of different projection devices.

Controllability or Temporal Variability:

This aspect represents a particularly important class of preferred embodiments, however, it is not mandatory.

REFERENCES

[1] R. O. Duda and P. E. Hart. *Pattern Classification and Scene Analysis*. Wiley, N.Y., 1973

[2] S. Haykin. Neural Networks. Prentice Hall Inc., Upper Saddle River, N.J., 1999.

[3] J. Hertz, A. Krogh, R. G. Palmer. *Introduction to the theory of neural computation*. Addison Wesley, Redwood City, Calif., 1991.

[4] E. Kraft, P. Fischer, M. Karagounis, M. Koch, H. Krüger, I. Peric, N. Wermes, C. Herrmann, A. Nascetti, M. Overdick, W. Rütten: Counting and Integrating Readout for Dirct Conversion X-ray Imaging. Concept, Realization and First Prototype Measurements. IEEE 2005 Nuclear Science Symosium Conference Record, pp 2761-2765, 0-7803-9221-3/05 (2005)

[5] Michael Athanassios Karagounis: Entwicklung analoger integrierter Schaltungen für Pixeldetektoren. Diplomarbeit. Fernuniversität Hagen, Fachbereich Elektrotechnik and Informationstechnik

[6] Y. Cheng, J. Zhang, Y. Z. Lee, B. Gao, S. Dike, W. Lin, J. P. Lu, O. Zhou: Dynamic radiography using a carbon-nanotube-based field-emission x-ray source. Review of Scientific Instruments (American Institute of Physics), Vol. 75, No. 10, pp. 3264-3267, October 2004, DOI: 10.1063/1.1791313

The invention claimed is:

1. Method for display of multi-channel image data for viewing by a user, wherein multi-channel image data of an object that are provided by multiple channels of single-channel image data of an imaging device are received, the multi-channel image data comprising image data for a plurality of pixels, each pixel represented by a data set of two or more data values, each data value of a respective pixel data set being associated with a respective single channel of the multiple channels of single-channel image data;

an image synthesis is performed on the basis of weighting the single-channel image data of the multi-channel image data in order to generate a synthesized image data set, the synthesized image data set comprising image data for a plurality of pixels of a synthesized image, each pixel of the synthesized image data set corresponding to a respective pixel of the multi-channel image data, and the synthesized image data set is output on a display device, the display device displaying the pixels of the synthesized image, the image synthesis being performed in a way that the data values of the data set of each pixel of the multi-channel image data are weighted and temporally oscillated at an oscillation frequency according to an alpha-blending function independent of the data sets of the other pixels of the multi-channel image data to calculate the value of the corresponding pixel in the synthesized image;

wherein the alpha-blending function for each data set comprises a respective alpha-blending function for each data value of the data set, the oscillation frequency and weighting of each respective alpha-blending function being controllable by a user during the output of the synthesized image data set on the display device.

2. Method as set forth in claim 1, where the multichannel image data are entered into an identifier that computes estimates for location-specific chemical, physical, or biological properties of the examined object, specifically for the location-specific presence and/or location-specific concentration of specific substances.

3. Method as set forth in claim 2, where, on the basis of single-channel raw data or single-channel image data, the value of a pixel of the synthesized image is further modified by the identification of the corresponding pixel in the multi-channel image data by the identifier.

4. Method as set forth in claim 3, wherein the identification of the corresponding pixel in the multi-channel image data by the identifier is generated on the basis of more than one single-channel raw data set or one single channel image data set.

5. Method as set forth in claim 2, wherein values of one or more pixels of the synthesized image are further modified on the basis of the output of the identifier.

6. Method as set forth in claim 1, where the received multi-channel image data are raw data or from raw data reconstructed image data.

7. Method as set forth in claim 1, where the received image data are generated by:
Computer tomography, specifically Multiple or Dual Source computer tomography or computer tomography with energy-resolving detectors,
Magnetic resonance imaging, specifically if different acquisition sequences or sequence parameters are applied,
Positron Emission Tomography,
Single Photon Emission Tomography,
Sonography by ultrasound,
Projection radiography,
Optical coherence tomography,
Multispectral optical image acquisition, specifically also in the infrared and ultraviolet domain,
Methods or devices for X-ray detection by charge integration and/or photon counting,
Methods or devices for the generation of X-rays that do not require a thermoelectric emission of electrons from a cathode material, or
Combinations of the aforementioned imaging modalities or dynamic, i.e. temporally repeated applications of the afore mentioned imaging modalities.

8. Method as set forth in claim 1 wherein the display of the synthesized image data is performed on the monitor of a viewing station of a PACS system.

9. Method as set forth in claim 1, wherein it is indicated during the display of the synthesized image data, that it is synthesized image data, or parameters of the image synthesis or input data utilized for the image synthesis or their type or properties are displayed.

10. A device for display to a user of pixels of an image synthesized from multi-channel image data comprising:
an appliance for receiving multi-channel image data of an object that are provided by multiple single-channel data channels of an imaging device, the multi-channel image data comprising image data for a plurality of input pixels, each input pixel represented by a set of data values, each set of data values containing more than one data value, each data value of a respective input pixel data set being associated with a respective single channel of the multiple channels of single-channel image data;
a computation unit for the execution of an image synthesis which is performed on the basis of the multi-channel image data in order to generate a pixel value of each pixel of a synthesized image, and
an output unit for the display of the synthesized image,
the computation unit being configured to apply weights to and temporally oscillate the values of the data set of each input pixel according to an alpha-blending function to generate the value of a corresponding pixel of the synthesized image; and
wherein the alpha-blending function associated with each data set comprises a respective alpha-blending function for each data value of the data set, the oscillation frequency and weighting of each of the respective alpha-blending functions of the data set being controllable by a user during the output of the synthesized image data set on the display device.

11. Device as set forth in claim 10, where the multichannel image data are entered into an identifier that computes estimates for location-specific chemical, physical, or biological properties of the examined object, specifically for the location-specific presence and/or location-specific concentration of specific substances.

12. Device as set forth in claim 11, where, on the basis of single-channel raw data or single-channel image data, a visualization data set is generated that is used together with the output of the identifier to synthesize image data.

13. Device as set forth in claim 12, where the visualization data set is generated on the basis of more than one single-channel raw data set or one single channel image data set.

14. Device as set forth in claim 11, where values of one or more pixels of the synthesized image are further modified on the basis of the output of the identifier.

15. Device as set forth in claim 10, where the received multi-channel image data are raw data or from raw data reconstructed image data.

16. Device as set forth in claim 10, where the received image data are generated by:
Computer tomography, specifically Multiple or Dual Source computer tomography or computer tomography with energy-resolving detectors, Magnetic resonance imaging, specifically if different acquisition sequences or sequence parameters are applied, Positron Emission Tomography, Single Photon Emission Tomography, Sonography by ultrasound, Projection radiography, Optical coherence tomography, Multispectral optical image acquisition, specifically also in the infrared and ultraviolet domain, Methods or devices for X-ray detection by charge integration and/or photon counting, Methods or devices for the generation of X-rays that do not require a thermoelectric emission of electrons from a cathode material, or Combinations of the aforementioned imaging modalities or dynamic, i.e. temporally repeated applications of the afore mentioned imaging modalities.

17. Device as set forth in claim 10, where the display of the synthesized image data is performed on the monitor of a viewing station of a PACS system.

18. Device as set forth in claim 10, where it is indicated during the display of the synthesized image data, that it is synthesized image data, or parameters of the image synthesis or input data utilized for the image synthesis or their type or properties are displayed.

19. A computer software product that includes a non-transitory storage medium readable by a processor, the non-transitory storage medium having stored thereon a set of instructions for performing a method for generating a display of multi-channel image data to a user, the instructions comprising:

(a) a first sequence of instructions which, when executed by the processor, causes the processor to perform an image synthesis algorithm on multi-channel image data and generating a synthesized image data set thereby, the multi-channel image data comprising image data for a plurality of pixels, each pixel represented by a set of data values, the set of data values containing more than one data value, each data value of a respective pixel data set being associated with a respective single channel of the multiple channels of single-channel image data, the image synthesis algorithm comprising a respective alpha-blending function associated with each set of data values that weights and temporally oscillates at an oscillation frequency the values of the data set associated with the alpha-blending function and thereby generating a value of a corresponding pixel of the synthesized image, wherein the alpha-blending function associated with each pixel of the multi-channel image data is independent of the other pixels of the multi-channel image data;

(b) a second sequence of instructions which, when executed by the processor, causes the processor to receive multi-channel image data of an object, the multi-channel image data comprising multiple single-channel image data provided by an imaging device, the multi-channel image data comprising image data for a plurality of pixels, each pixel represented by a set of data values, the set of data values containing more than one data value, each data value of a respective pixel data set being associated with a respective single channel of the multiple channels of single-channel image data;

(c) a third sequence of instructions which, when executed by the processor, causes the processor to execute the image synthesis algorithm utilizing a plurality of alpha-blending functions, each alpha-blending function associated with a respective data set of the multi-channel image data and generating a value of a corresponding pixel of a first synthesized image data set thereby, each alpha-blending function weighting and oscillating at an oscillating frequency each of the data values of the data set associated with the alpha-blending function to generate the value of the corresponding pixel, each alpha-blending function being independent of the other alpha-blending functions;

the third set of instructions further comprising instructions which, when executed by the processor, causes the processor to execute for each alpha-blending function a respective alpha-blending function for each data value of the data set, the alpha-blending function for each data value independent of the other alpha-blending functions of the other data values of the data set;

(d) a fourth sequence of instructions, which, when executed by the processor, causes the processor to send the first synthesized image data set to a display device;

(e) a fifth sequence of instructions, which, when executed by the processor after the processor sends the first synthesized image data set to the display device causes the processor to receive user input related to one of the pixels of the first synthesized image data set changing either or both of the weighting and oscillation frequency of one of the alpha-blending functions associated with the data values of the corresponding pixel of the multi-channel image data;

(f) a sixth sequence of instructions, which, when executed by the processor after receiving the user input, causes the processor to re-execute the image synthesis algorithm utilizing the alpha-blending function as modified by the user input and generating a second synthesized image data set thereby; and (g) a seventh sequence of instructions, which, when executed by the processor after generating the second synthesized image data set, sends the second synthesized image data set to the display device.

20. The computer software product of claim 19 wherein the non-transitory storage medium includes an eighth sequence of instructions, which, when executed by the processor, sends multichannel image data to an identifier that utilizes the multichannel image data to compute estimates for location-specific chemical, physical, or biological properties of the object.

21. The computer software product of claim 19 wherein the non-transitory storage medium includes an eighth sequence of instructions, which, when executed by the processor, generates a visualization data set utilizing the single-channel image data.

22. The computer software product of claim 19 wherein the non-transitory storage medium includes an eighth sequence of instructions, which, when executed by the processor, causes the processor to send data representing the weighting and the oscillation frequency of one or more of the alpha-blending functions used in generating the synthesized image data set being sent to the display device.

* * * * *